United States Patent [19]

Freeman et al.

[11] Patent Number: 5,683,809
[45] Date of Patent: Nov. 4, 1997

[54] BARRIER ELEMENT FABRICS, BARRIER ELEMENTS, AND PROTECTIVE ARTICLES INCORPORATING SUCH ELEMENTS

[75] Inventors: Walter J. Freeman, Social Circle; Rakesh K. Gupta, Rockdale County; James H. Harrington, Stone Mountain; Richard J. Legare, Newton County; Thomas L. Smith, Snellville; Adrienne W. Williams, Stone Mountain, all of Ga.

[73] Assignee: Hercules Incorporated, Wilmington, Del.

[21] Appl. No.: 238,324

[22] Filed: May 5, 1994

[30] Foreign Application Priority Data

Aug. 23, 1993 [GB] United Kingdom ............... 93-174902

[51] Int. Cl.$^6$ ........................................ D02G 3/00
[52] U.S. Cl. ................... 428/365; 428/284; 428/286; 428/288; 428/297; 428/323; 428/248; 428/340; 428/357; 428/401; 604/372
[58] Field of Search ........................ 428/401, 284, 428/288, 286, 287, 298, 323, 219, 340, 360, 365, 308.2, 296, 357, 172, 247; 128/846; 604/369, 370, 371, 372, 373, 374

[56] References Cited

U.S. PATENT DOCUMENTS

| | | |
|---|---|---|
| 2,668,785 | 2/1954 | Jefferson et al. . |
| 2,751,962 | 6/1956 | Drummond . |
| 2,983,625 | 5/1961 | Schappel . |
| 3,388,028 | 6/1968 | Alexander ................ 161/156 |
| 3,768,480 | 10/1973 | Mesek et al. . |
| 3,821,021 | 6/1974 | McMillin ................ 117/135.5 |
| 3,936,555 | 2/1976 | Smith, II . |
| 3,983,272 | 9/1976 | Huber et al. . |
| 4,010,752 | 3/1977 | Denny . |
| 4,059,114 | 11/1977 | Richards . |
| 4,097,943 | 7/1978 | O'Connell . |
| 4,105,381 | 8/1978 | Platt et al. . |
| 4,196,245 | 4/1980 | Kitson et al. . |
| 4,223,677 | 9/1980 | Anderson ................ 128/287 |
| 4,397,644 | 8/1983 | Matthews et al. . |
| 4,480,000 | 10/1984 | Watanabe et al. ................ 428/284 |
| 4,508,113 | 4/1985 | Malaney . |
| 4,519,799 | 5/1985 | Sakurai et al. . |
| 4,555,811 | 12/1985 | Shimalla . |
| 4,560,372 | 12/1985 | Pieniak . |
| 4,623,575 | 11/1986 | Brooks et al. . |
| 4,627,848 | 12/1986 | Lassen et al. . |
| 4,652,484 | 3/1987 | Shiba et al. . |
| 4,657,539 | 4/1987 | Hasse . |
| 4,657,804 | 4/1987 | Mays et al. . |
| 4,673,402 | 6/1987 | Weisman et al. . |
| 4,725,473 | 2/1988 | Van Gompel et al. ................ 428/156 |
| 4,753,834 | 6/1988 | Braun et al. . |
| 4,755,178 | 7/1988 | Insley et al. . |
| 4,767,586 | 8/1988 | Radwanski et al. . |
| 4,781,962 | 11/1988 | Zamarripa et al. . |
| 4,798,603 | 1/1989 | Meyer et al. ................ 604/378 |
| 4,808,467 | 2/1989 | Suskind et al. . |
| 4,816,025 | 3/1989 | Foreman . |
| 4,822,668 | 4/1989 | Tanaka et al. . |
| 4,837,078 | 6/1989 | Harrington . |
| 4,846,824 | 7/1989 | Lassen et al. . |
| 4,868,031 | 9/1989 | Modrak et al. . |
| 4,883,707 | 11/1989 | Newkirk ................ 428/119 |
| 4,886,697 | 12/1989 | Perdelwitz, Jr. et al. . |
| 4,892,534 | 1/1990 | Datta et al. ................ 604/370 |
| 4,892,596 | 1/1990 | Kielpikowski et al. . |
| 4,892,598 | 1/1990 | Stevens et al. . |
| 4,904,520 | 2/1990 | Dumas et al. . |
| 4,931,357 | 6/1990 | Marshall et al. . |
| 4,938,832 | 7/1990 | Schmalz . |
| 5,019,066 | 5/1991 | Freeland et al. . |
| 5,033,172 | 7/1991 | Harrington . |
| 5,045,387 | 9/1991 | Schmalz . |
| 5,057,357 | 10/1991 | Winebarger . |
| 5,108,827 | 4/1992 | Gessner . |
| 5,192,606 | 3/1993 | Proxmire et al. ................ 428/284 |
| 5,221,573 | 6/1993 | Baigas, Jr. . |
| 5,229,191 | 7/1993 | Austin ................ 428/198 |
| 5,257,982 | 11/1993 | Cohen et al. . |
| 5,281,378 | 1/1994 | Kozulla . |
| 5,288,348 | 2/1994 | Modrak . |
| 5,294,482 | 3/1994 | Gessner . |
| 5,298,694 | 3/1994 | Thompson et al. . |
| 5,318,735 | 6/1994 | Kozulla . |
| 5,393,812 | 2/1995 | Haley et al. . |
| 5,431,994 | 7/1995 | Kozulla . |
| 5,534,340 | 7/1996 | Gupta et al. . |

FOREIGN PATENT DOCUMENTS

| | | |
|---|---|---|
| 2053831 | 6/1992 | Canada . |
| 2089401 | 8/1993 | Canada . |
| 2104281 | 11/1994 | Canada . |
| 0157649 | 10/1985 | European Pat. Off. . |
| 0159671 | 10/1985 | European Pat. Off. . |
| 0210968 | 2/1987 | European Pat. Off. . |

(List continued on next page.)

OTHER PUBLICATIONS

"Automated Determination of Pore vol. Distrubutions and Related Properties," Textile Research Instutute (TRI) Notes on Research, Dr. H.G. Heiweil, Ed., Article No. 464, Sept. 1992.

Cohen, "A Wet Pore–Size Model For Coverstock Fabrics," Hercules, Incorporated, INDA Book of Papers, Baltimore, MD (1990).

AATCC 1952-18.

ASTM D–1117–79.

ASTM D–4120–90, "Standard Test Method for Fiber Cohesion in Roving, Sliver, and Top (Dynamic Tests)".

(List continued on next page.)

Primary Examiner—Merrick Dixon
Attorney, Agent, or Firm—Mark D. Kuller

[57] ABSTRACT

Protective articles such as diapers, having filmless hydrophobic barrier elements such as cuffs and backing sheets. The barrier cuffs—which can be, for instance, leg cuffs and waistbands—and the backing sheets can be provided from fabrics having a fabric weight of at least 10 gsy; these fabrics are made of cardable, hydrophobic polyolefin fibers having a dpf value of not more than about 2.0.

37 Claims, No Drawings

FOREIGN PATENT DOCUMENTS

| | | |
|---|---|---|
| 0175481 | 9/1987 | European Pat. Off. . |
| 0254476 | 1/1988 | European Pat. Off. . |
| 0296572 | 12/1988 | European Pat. Off. . |
| 0325416 | 7/1989 | European Pat. Off. . |
| 0367989 | 5/1990 | European Pat. Off. . |
| 0399511 | 11/1990 | European Pat. Off. . |
| 0445536 | 9/1991 | European Pat. Off. . |
| 0486158 | 5/1992 | European Pat. Off. . |
| 0490476 | 6/1992 | European Pat. Off. . |
| 0516412 | 12/1992 | European Pat. Off. . |
| 0838047 | 4/1993 | European Pat. Off. . |
| 0552013 | 7/1993 | European Pat. Off. . |
| 0557024 | 8/1993 | European Pat. Off. . |
| 0619393 | 10/1994 | European Pat. Off. . |
| 0620294 | 10/1994 | European Pat. Off. . |
| 0621356 | 10/1994 | European Pat. Off. . |
| 0630996 | 12/1994 | European Pat. Off. . |
| 828735 | 2/1960 | United Kingdom . |
| 2087240 | 5/1982 | United Kingdom . |
| 2124907 | 2/1984 | United Kingdom . |

OTHER PUBLICATIONS

ASTM D–1117–80.

Legare, "Thermal Bonding of Polypropylene Fibers in Nonwovens," 1986 TAPPI Synthetic fibers for Wet System and Thermal Bonding Applications, Boston, MA, Oct. 9–10, 1986.

English Language Abstract of JP 3241049.

English Language Abstract of JP 3241051.

ASTM D–4120–82, "Standard Test Method for Fiber Cohesion in Roving, Sliver and Top (Dynamic Tests)".

Pirkkanen, "Multi–Layer Nonwovens For Coverstock, Medical, and Other End Uses," *Nonwovens World*, Nov. 1969.

Smith, "Multilayer Diaper Coverstocks Offer New Opportunities," *Nonwovens World*, Jul. 1988.

Smith et al., "Polypropylene Thermal Bonding Fibers; That Was Then—This is Now," INDATEC 91 – Apr. 11, 1991.

European Search Report and Annex.

English Language Abstract of Japanese Patent Publication No. 43–33651.

English Langauge Abstract of Japanese Patent Publication No. 43–33652.

BARRIER ELEMENT FABRICS, BARRIER ELEMENTS, AND PROTECTIVE ARTICLES INCORPORATING SUCH ELEMENTS

BACKGROUND OF THE INVENTION

1. Field of the Invention

The present invention relates to barrier element fabrics and barrier elements prepared from such fabrics, as well as to the preparation of these fabrics and barrier elements, and to protective articles incorporating these elements.

2. Description of Background and Other Information

Various configurations of waste containment garments and barrier cuffs are known in the art. Further, different fibers, fabrics and finishes—e.g., hydrophobic fibers, fabrics and finishes—are also known.

U.S. Pat. Nos. 4,657,539 and 4,816,025 both disclose waste containment barrier cuffs which can be prepared from different materials, including polypropylene. U.S. Pat. No. 4,657,539 further discloses leg cuffs of material having a basis weight of about 30 to about 150 grams per square meter (gsm), prepared from filaments having a denier of from about 6 to about 15, and specifies a leg cuff member having a basis weight of about 65 grams per square yard (gsy), or 77.7 gsm. U.S. Pat. No. 4,816,025 refers to the barrier cuffs disclosed therein as preferably being hydrophobic, and more preferably liquid impermeable, and rendered so in any manner well known in the art—such as selectively treating the barrier cuffs, untreating the barrier cuffs, or by securing a separate material to the barrier cuffs.

European Patent Application 0 486 158 refers to a particularly troublesome technical problem as arising, when a high degree of hydrophobicity is desired on cuffs or borders in a diaper or similar product, produced from polyolefin-containing staple. The problem is indicated to arise from untreated fiber becoming unworkable during processing, while various finishes make the fiber workable, but render it unsuitably hydrophilic. Use of a fiber treatment, involving application, as part of the treatment components, of a neutralized phosphoric acid ester as an antistat, is indicated to render the fibers processable, without undue loss of hydrophobicity. Mention is made of polyolefin fiber webs, from fiber not exceeding about 40 dpf, and preferably within a range of about 0.1–40dpf; staple prepared from 2.0–2.54dpf filaments is specifically disclosed. Cover stock is indicated to vary in weight from about 10–45 gm yd$^2$, or higher.

Canadian Patent Publication 2,089,401 refers to the desirability of hydrophobic fibers, for nonwoven polyolefin fabrics in applications such as diaper leg cuffs and waistbands. Also disclosed therein is a fiber having a finish comprising an antistatic composition, and, with the finish, having a hydrostatic head value of at least 102 mm; the fiber is further characterized as preferably about 0.1 to 40 dpf, more preferably about 1 to 6 dpf, and most preferably about 1.8 to 3 dpf. Fabric, formed from the fiber, is indicated to have a preferred basis weight of about 10–60 gsy; more preferably 10–30, and, most preferably, 10–25 gsy. 1 to 6 dpf fibers are indicated to be preferred, and 1.8 to 3 dpf fibers are indicated to be most preferred, for use in hydrophobic fabrics useful as leg cuffs and waistbands of diapers.

U.S. Pat. No. 4,938,832 discloses a method for placing hydrophobic polyolefin fiber in condition for cutting, carding and production of nonwoven material, without substantial sacrifice of hydrophobic properties in the corresponding nonwoven, by subjecting the fiber to treatment which—as discussed with respect to European Patent Application 0 486 158—involves application of a neutralized phosphoric acid ester as an antistat.

European Patent Application 0 516 412 discloses treating the surface of hydrophobic polyolefin fibers—to improve their lubricity and antistatic properties, and to facilitate processing them into hydrophobic nonwoven articles—by application of a specified polyol or polyol derivative, and a neutralized phosphoric acid ester.

U.S. Pat. No. 3,983,272 discloses a method for improving the lubricity and antistatic properties of organic fibers comprising coating the fibers with a composition containing a poly(diorganosiloxane), a phosphorous compound capable of imparting antistatic properties to the fibers, and, if desired, paraffin waxes.

U.K. Patent Specification 828,735 discloses a process for lubricating hydrophobic filaments made from synthetic linear hydrocarbon polymers, particularly polypropylene, containing a major proportion of the polymer in isotactic form, characterized in that the filaments are brought into contact with an aqueous solution of at least one polymeric substance containing recurring oxyalkylene units.

It has been discovered that filmless hydrophobic fabrics, comprising cardable, hydrophobic polyolefin fibers, have particular utility for barrier elements of protective articles. Barrier elements thusly lacking films are characterized by several advantages.

For example, in many instances it is preferable for the protective article to have a textile clothlike feel rather than a "filmy" feel. This is true for protective garments, including waste containment articles and especially diapers. The filmless barrier elements of the invention are characterized by a clothlike, softer, better feel than is provided by the coated elements of the prior art; particularly, the lower the denier of the fiber from which the barrier element of the invention is prepared, the softer its feel.

Moreover, omission of the film saves expense and time. Capital costs are lowered and energy is conserved, while material which would have been required for the film is likewise saved, and waste is correspondingly lessened. Additionally, an entire step is saved in processing, and potential mistakes from application of the film are avoided.

Yet additionally, use of lower fiber denier, or use of fibers of differing deniers with at least one of the deniers being a lower denier, provides further advantages in the barrier element fabrics of the invention. It has been discovered that where fabric weight is kept constant and uniformity remains at least comparable, the indicated lower or mixed/lower fiber denier decreases pore size, while increasing the hydrostatic head of the barrier element fabrics of the invention, and also increasing the fabric average tensile property. Further, use of such lower or mixed/lower fiber denier also increases the fabric uniformity.

SUMMARY OF THE INVENTION

The invention pertains to a protective article which comprises a filmless hydrophobic barrier element. This barrier element comprises a nonwoven fabric, and the fabric comprises carded and bonded hydrophobic polyolefin staple fibers.

In a first preferred embodiment, the barrier element fabric has a fabric weight of at least about 10 gsy, and substantially all of the staple fibers have a dpf value of not more than about 2.0. In a second preferred embodiment, the fabric has a water hydrostatic head value of at least about 60 mm, and at least about 10 percent by weight of the staple fibers have a dpf value of not more than about 2.0. In a third preferred embodiment, the fabric has an average pore size of not more than about 52 microns.

Preferably, the indicated polyolefin of the fibers is polypropylene. Also as a matter of preference, the protective article of the invention is a waste containment article, and the barrier element comprises at least one member selected from the group consisting of barrier cuffs and a fluid-impervious backing component. Particularly preferred waste containment articles of the invention are diapers, wherein the barrier elements are provided as one or more of waistbands, leg cuffs, and such backing components or sheets.

DESCRIPTION OF THE INVENTION

The term "filmless", as used herein in conjunction with the barrier elements and fabrics of the invention, refers to the absence of a lamination or a coating layer—such as a plastic film—covering the barrier elements and fabrics. In this regard, such films and layers include those obtained by extrusion coating of the film or layer material onto the fabric, by such means as hot melt extrusion—wherein the coating material can thusly be applied to the fabric in fluid form, for solidification into the indicated film or layer.

However, "filmless" does not exclude the presence of plural fabrics, such as two or more fabrics situated as multiple layers. Further, "filmless" does not entail or require the lack of a surface treatment—e.g., such as application of a finish—to the cuffs and fabrics of the invention, and/or to fibers comprising these cuffs and fabrics. Accordingly, the filmless cuffs and fabrics of the invention, and fibers from which these cuffs and fabrics are prepared, include those which have been the subject of such surface treatment. For instance, consistent with the discussion herein, the fibers and fabrics of the invention include those comprising, or treated with, a hydrophobic finish—particularly, a hydrophobic antistatic finish.

Discussion herein of pore size is understood as referring to average pore radius.

Further, fabric pore size, as discussed herein, is determined according to the procedure as set forth in "Automated Determination, of Pore Volume Distributions and Related Properties", Textile Research Institute (TRI) Notes on Research, Dr. H. G. Heilweil, Ed., Article No. 464, September, 1992, which is incorporated herein in its entirety, by reference thereto. Measurements can be taken, using the TRI wettability apparatus or Gravimetric Absorbency System (GATS).

In this procedure, the measurement of pore size distribution entails filling the voids of a fabric to capacity, with a liquid which makes a low receding contact angle. The total liquid volume uptake is then determined for the filled fabric, and a stepwise pressure gradient is applied thereto by raising the wetting chamber.

The liquid recedes only from the voids which are larger than the critical pore size (R) at a given difference in applied pressure (ΔP). This result is expressed by the LaPlace equation, which is as follows:

$$R = \frac{2\gamma \cos\Theta}{\Delta P}$$

where $\gamma$ is the liquid surface tension, and $\Theta$ is the receding contact angle.

Consistent with the foregoing, fabric pore size can be calculated from the density of the fabric and the denier of the fibers (or deniers, where fibers of different deniers are used, and the relative proportions of the different denier fibers is known) comprising the fabric—according to the method disclosed in Cohen, "A Wet Pore-Size Model for Coverstock Fabrics", Hercules Incorporated, INDA Book of Papers, Baltimore, Md. (1990); this article is incorporated herein in its entirety, by reference thereto. Using the model generated by this method, which also employs the GATS as discussed herein, different combinations of fabric density and fiber denier can be determined for providing a desired pore size.

The fabrics of the invention comprise, consist essentially of, or consist of cardable, hydrophobic fibers; i.e., the fibers are staple fibers. Staple fibers of the invention are preferably about 1 to 6 inches, more preferably about 1 to 3 inches, still more preferably about 1¼ to 2 inches in length.

Also as a matter of preference, the fibers comprise, consist essentially of, or consist of polyolefin fibers.

Among those polyolefins which may be used are homopolymers and copolymers. In this context, the copolymers are understood as including both those polymers incorporating two different monomeric units, as well as polymers incorporating three or more different monomeric units, e.g., terpolymers, etc.

It is further understood that reference to a polymer of any particular monomeric unit—e.g., reference to a particular polyolefin—encompasses the presence of one or more yet additional components, in addition to the named monomer. For example, polypropylene often comprises up to about 10 weight percent of one or more other monomeric units—particularly olefin units—such as ethylene, butene, etc.

Whether any such additional material is indeed present, and the amounts thereof, can be a matter of intentional design, for a specified purpose or purposes—e.g., one or more desired properties, of the ultimately obtained fiber or filament. Further, the presence and amounts of such additional material can be because of fortuitous circumstances —e.g., the purity of what is available for use.

Polyolefins of the invention include the crystalline polyolefins. Examples of homopolymers which may be used are those of propylene, ethylene, butene, and pentene. Copolymers of the invention are those including one or more of the indicated propylene, ethylene, butene, and pentene as comonomers; for such copolymers, further olefins suitable as comonomers include those as known in the art, such as 1-butene, 2-butene, isobutylene, hexene, heptene, octene, 2-methylpropene-1, 3-methylbutene-1, 4-methylpentene-1, 4-methylhexene-1, 5-methylhexene-1, bicyclo-(2,2,1)-2-heptene, styrene, and methylstyrene. The comonomers are included in the amounts known in the art.

A single polyolefin or two or more polyolefins may be employed, in whatever relative amounts are suitable for obtaining a product characterized by the properties desired for a particular purpose. One or more other polymers can be employed, together with the one or more polyolefins.

Preferred polyolefins are those polypropylenes (PP) and polyethylenes (PE), including the low density polyethylenes (LDPE), high density polyethylenes (HDPE), and linear low density polyethylenes (LLDPE), which are suitable for the cardable, hydrophobic fibers of the invention. Further preferred polyolefins, among the copolymers, are those ethylene-propylene copolymers, including block copolymers of ethylene and propylene, and random copolymers of ethylene and propylene, which are likewise appropriate.

The fibers of the invention may be provided in monocomponent configurations, multicomponent (e.g., bicomponent) configurations, including conventional sheath/core and side-by-side multicomponent configurations, and multiconstituent (e.g., biconstituent)

configurations. Where there are multiple polymers (including the indicated one or more polyolefins) present, any suitable combinations of the polymers, including the multicomponent and multiconstituent configurations, can be employed. The types and proportions of the polymers used can be readily determined by those of ordinary skill in the art, without undue experimentation.

Particular suitable polyolefin hydrophobic fibers include polyethylene, polypropylene, polyethylene/polypropylene bicomponent fibers, polyethylene/polyester bicomponent fibers, polyethylene/polypropylene alloys, polypropylene/polyethylene biconstituent fibers, polyethylene/polypropylene-polyethylene copolymer biconstituent fibers, and any combination of these fibers. The preferred hydrophobic fibers are polypropylene fibers.

Commercially available polypropylenes which may be used include Himont 20MFR, 10 MFR, and 12 MFR, from Himont U.S.A., Wilmington, Del., and Amoco 4 MFR and 9 MFR pellets, from Amoco Chemical Company, Chicago, Ill. These polymers have the properties as indicated below.

| Polymer | Type | Density[1] g/cm3 | Melt[2] Flow dg/min | Melting Point Range (°C.) |
|---|---|---|---|---|
| Himont 20 MFR | PP | .905 | 20 | 160–165 |
| Himont 10 MFR | PP | .905 | 10 | 160–165 |
| Himont 12 MFR | PP | .905 | 13 | 160–165 |
| Amoco 4 MFR | PP | .905 | 4 | 160–165 |
| Amoco 9 MFR | PP | .905 | 9 | 160–165 |

[1]ASTM D792
[2]ASTM 1238.230° C.

Preferred fibers, and methods for their preparation, include those as disclosed in Canadian Patent Publication 2,089,401, in European Patent Applications 0 486 158 and 0 516 412, in U.S. Pat. Nos. 4,938,832 and 5,281,378, and in U.S. applications Ser. Nos. 07/474,897, filed Feb. 5, 1990, 07/683,635, filed Apr. 11, 1991 (allowed), 07/818,772, filed Jan. 13, 1992, 07/887,416, filed May 20, 1992, 07/939,857, filed Sep. 2, 1992 (allowed), 07/943,190, filed Sep. 11, 1992, 08/003,696, filed Jan. 13, 1993, 08/016,346, filed Feb. 11, 1993, 08/046,861, filed Apr. 16, 1993, 08/047,407, filed Apr. 19, 1993, and 08/145,360, filed Oct. 29, 1993. These patent publications and these applications are incorporated herein in their entireties, by reference thereto.

The fibers may be provided in any configuration or combination of configurations suitable for the intended purpose of the invention. Among those which may be employed are the indicated multiconstituent and multicomponent configurations, and the circular, rectangular, dogbone, delta, trilobal, and diamond cross-sectional configurations—as well as two or more of these.

Preferably, the fibers of the invention are hydrophobic, and thermally bondable. Also as a matter of preference, the fibers of the invention are cardable—preferably, at commercial rates—so as to be suitable for preparing fabrics therefrom—particularly, nonwoven fabrics, of the invention.

One means for rendering the fibers of the invention cardable, while providing or retaining hydrophobicity, is by treating these fibers with one or more suitable hydrophobic finishes—particularly, suitable hydrophobic antistatic finishes—the application of which, to the fibers, will result in the fibers being characterized by the indicated cardability and hydrophobicity. The requisite finish compositions can be applied to the fibers and fabrics at the appropriate point during their preparation—e.g., consistent with the discussion herein, before, during, or after one or more of the extrusion, drawing, and crimping stages, of fiber preparation.

Appropriate such finishes, and treatments for application of such finishes, include those as disclosed in Canadian Patent Publication 2,089,401, in European Patent Applications 0 486 158, and 0 516 412, in U.S. Pat. No. 4,938,832, and in U.S. application Ser. No. 08/016,346, filed Feb. 11, 1993.

Correspondingly, the fabrics of the invention are likewise preferably hydrophobic, and also preferably nonwicking. Further, the fabrics of the invention have particular utility for barrier elements, especially hydrophobic barrier elements, for protective articles. Particularly—without application of a film thereto, as discussed herein—they have particular utility for correspondingly filmless hydrophobic barrier elements for protective articles.

Included among the protective articles of the invention are barrier protective garments, including shirts, pants, jackets, coats, and especially hospital and surgical caps, gowns, and scrub apparel, as well as sheets, surgical table and Mayo stand covers, industrial garments, etc. Preferred protective articles of the invention are hygiene products, e.g., waste containment articles; suitable waste containment articles include diapers—particularly, disposable diapers (including adult diapers)—and sanitary protection articles, such as catamenial devices, incontinence pads, and the like.

The barrier elements of the invention are elements for slowing, inhibiting or preventing the passage of materials—such as fluids, and wastes—therethrough or thereby. Suitable such barrier elements include borders, barrier cuffs, and backings, particularly waistbands and leg cuffs.

Consistent with the foregoing, particularly preferred protective articles of the invention are waste containment articles, and correspondingly particularly preferred barrier elements therefor are barrier cuffs—especially leg cuffs and waistbands—and backings—especially fluid impervious backing components.

Waste containment articles, including those of the invention, generally include a fluid-impervious backing component, a body-contacting surface (which may be defined by a nonwoven-type fabric or coverstock material), and a fluid-adsorbing component (i.e, core components such as are well known in the art).

The fluid-adsorbing component is preferably a core component, situated between the body-contacting surface and the fluid-impervious backing component. Also as a matter of preference, the fluid-adsorbing component comprises one or more layers of compressed absorbent material, such as wood pulp, rayon, gauze, tissue, or the like—and in some cases, synthetic hydrophilic material such as superabsorbent powder.

The protective article of the invention comprises a filmless hydrophobic barrier element, which in turn comprises a nonwoven fabric. This fabric comprises, or consists essentially of, or consists of carded and bonded hydrophobic polyolefin staple fibers.

The barrier element fabric may be a single fiber layer or web. Alternatively, as discussed herein, this fabric may be prepared from two or more layers or webs of fibers.

In a first preferred embodiment of the protective article of the invention, all or substantially all of the staple fibers of the barrier element nonwoven fabric have a dpf value of not more than about 2.0.

In a second preferred embodiment of the protective article of the invention, at least about 10 percent—more preferably at least about 20 percent, more preferably at least about 30 percent, still more preferably at least about 40 percent, still more preferably at least about 50 percent, still more preferably at least about 60 percent, still more preferably at least about 70 percent, and still more preferably at least about 80 per cent—by weight of the staple fibers of the barrier element nonwoven fabric have a dpf value of not more than about 2.0.

In a third preferred embodiment of the protective article of the invention, the barrier element nonwoven fabric has an average pore size of not more than about 52 microns—more preferably not more than about 51 microns, still more preferably not more than about 50 microns, still more preferably not more than about 43 microns, still more preferably not more than about 41 microns, still more preferably not more than about 30 microns, still more preferably not more than about 20 microns, and still more preferably not more than about 17 microns. As a particularly preferred range, the barrier element fabric of the invention has an average pore size of about 17 to 52 microns.

Where their barrier element fabrics are characterized by the features of more than one of the indicated first, second, and third embodiments, the protective articles of the invention can be considered as examples of any or all of such embodiments.

Particularly with respect to the first and second embodiments, the indicated dpf value for the staple fiber of barrier element fabric is more preferably about 1.9 or less. Still more preferably the indicated dpf value is about 1.8 or less, and yet still more preferably about 1.7 or less; most preferably, this dpf value is not more than about 1.6 or less. A corresponding preferred minimum dpf value in these embodiments is at least about 0.5—more preferably, at least about 0.65, still more preferably at least about 0.8, and most preferably at least about 1.0.

Also for the barrier element fabrics of the invention, including those of both the indicated first, second and third embodiments, the barrier element fabric may comprise fibers of two or more different dpf values, and in varying relative proportions of the different dpf values; this inclusion of differing dpf value fibers is particularly preferred for the second and third embodiments. The indicated single layer or web barrier element fabrics of the invention, thusly characterized by differing dpf value fibers, accordingly include such differing dpf value fibers in this single layer.

Regarding examples of fibers of differing dpf values, the barrier element fabric may be prepared from a combination of staple fibers wherein about 10 to 90 percent by weight of the fibers have a dpf value of about 0.5 to 2.0, and about 10 to 90 percent by weight of the fibers have a dpf value of about 2.2 to 4.0dpf. More particularly, the barrier element fabric may be prepared from a combination of staple fibers wherein about 10 to 90 percent by weight of the fibers have a dpf value of about 1.0 to 1.8, and about 10 to 90 percent by weight of the fibers have a dpf value of about 2.2 to 4.0 dpf. Particular such combinations which are suitable include those wherein the indicated lower denier fibers have a dpf value of any of 1.0 or 1.2 or 1.4 or 1.6 or 1.8, while the dpf value of the higher denier fibers is 2.2. Corresponding combinations of such 1.0, 1.2, 1.4, 1.6, or 1.8 dpf fiber with 3.0 dpf fiber are also suitable.

The combination of 1.6 and 1.0 dpf fibers is particularly preferred.

Also or in the alternative to comprising fibers of differing dpf values, the barrier element fabric of the invention—yet again, including those of the indicated first, second, and third embodiments—may include fibers of two or more different polymers and/or polymer blends or combinations —likewise, in varying proportions; for instance, different relative proportions of polypropylene fibers and polyethylene fibers may be employed. The indicated single layer or web barrier element fabrics of the invention, thusly characterized by fibers of different polymers and/or polymer blends or combinations, accordingly include such fibers of differing composition in this single layer.

Yet further as to the barrier element fabrics of the invention—including those of the indicated first, second, and third embodiments—these fabrics may be provided from two or more layers or webs of fibers. In this regard, composite fabrics, appropriately prepared from two or more layers or webs of fibers, are suitable as fabrics for the barrier elements of the invention.

For instance, a plurality of unbonded webs can be stacked to provide a multiple layer fabric, which is then subjected to bonding—preferably, by a thermal technique, as discussed herein. One method for providing such a multiple layer fabric is to successively deposit carded webs on a moving belt, with the thusly stacked layers then being bonded together.

Alternatively, the multiple layer barrier element fabric can be prepared by separately bonding the individual layers, then bonding the thusly previously bonded layers together in a separate, later step; here also, thermal bonding is suitable for both the initial and later steps. In the case of the indicated carded webs, each can be individually subjected to a bonding step, with the resulting layers then subsequently bonded together.

For barrier element fabrics of the invention thusly comprising multiple layers, one or more of the layers can include fibers of at least two different dpf values. Additionally or in the alternative, two or more of the indicated multiple layers can each comprise, consist essentially of, or consist of fibers of different dpf values—that is, the at least two layers of the multiple layer fabric can include a first layer with fibers of a first dpf value, and a second layer with fibers of a second, differing dpf value. For instance, as to the particular dpf value combinations discussed herein, the barrier element fabric can have two layers or webs, with one comprising fibers having a dpf value of about 1.0 to 1.8, and the other comprising fibers having a dpf value of about 2.2 to 4.0.

Preferred multiple layer barrier element fabrics of the invention are those consisting essentially of two layers, each layer prepared from fibers of differing dpf values.

Also or in the alternative to the multiple layers or webs comprising fibers of different dpf values, one or more of the layers or webs can include fibers of different polymers and/or polymer blends or combinations. Still additionally or in the alternative, two or more of the layers or webs can comprise fibers of different polymers and/or polymer blends or combinations. For instance, there can be two layers or webs, with one comprising polypropylene fibers and the other comprising polyethylene fibers.

Barrier element fabrics of the invention, including those of the first, second, and third embodiments, are preferably characterized by a fabric weight of at least about 10 gsy— more preferably, of at least about 15 gsy, and most preferably of at least about 18 gsy. As a preferred range, the barrier element fabrics of the invention have a fabric weight of about 10–50 gsy (this range being particularly preferred for the second embodiment of the invention); a more preferred range is about 15–30 gsy, and the most preferred range is about 18–23 gsy.

Barrier element fabrics of the invention, including those of the first, second, and third embodiments, are preferably characterized by a fabric density of about 0.01 to 0.15 g/cc. A more preferred range is about 0.05 to 0.15 g/cc, and a particularly preferred range is about 0.07 to 0.15 g/cc.

Pore size is a property affecting the efficacy, of the hydrophobic fabrics and barrier elements of the invention, in their intended function—i.e., as barriers against the passage of moisture. In this regard, the smaller the pore size, the greater the resistance to liquid penetration. Preferably, the pore size, of the barrier element fabrics of the invention, is such as to impart the property of "breathability"—specifically, small enough so as to inhibit the passage of liquids, but large enough to permit the passage of gases, particularly air.

Correspondingly, fiber denier, fabric weight, and fabric density are also features which can each affect the indicated moisture barrier function. Specifically, the finer the fibers —i.e., the smaller the fiber denier, or the lower the fiber dpf value—the more resistant the fabric is to the passage of liquid; this barrier effect is also increased by raising the fabric weight, and by increasing fabric density.

In this regard, fabric density can be affected by fabric weight. Specifically, fabric density is controlled by calender bonding pattern and fabric weight.

There are practical considerations limiting the fiber dpf value, fabric weight, and fabric density which can be attained and employed. However, with respect to the indicated effects of varying fiber dpf value, fabric weight, and fabric density, all three of these can be correspondingly manipulated in compensation for one another, so as to achieve a particular degree of barrier effect.

Particularly, dpf value and fabric weight can be thusly manipulated in compensation for one another, and dpf value and fabric density can be manipulated in compensation for one another. For instance, using fibers of higher dpf value can be compensated for by increasing fabric weight and/or fabric density, while, correspondingly, fabric of lighter weight and/or less density can be compensated for by the use of finer fibers.

Corresponding to the foregoing, and consistent with the discussion herein concerning calculation of fabric pore size, both fabric density—and accordingly, fabric weight—and fiber dpf value can likewise be employed to control fabric pore size. Specifically, decreasing fiber dpf value and increasing fabric density will each reduce pore size; increasing fabric density will also narrow pore size distribution.

Particularly, fiber dpf value—and accordingly, as indicated, fabric weight—and fabric density can be manipulated to obtain a particular pore size. Specifically, if the denier of the fiber is increased, then, so that the pore size is not also increased, the resulting fabric can be made with a greater fabric density—while, if the fabric density is reduced, compensation can be effected by decreasing fiber denier.

Accordingly, specific combinations of fiber dpf value and fabric density may be employed to obtain desired pore sizes for barrier element nonwoven fabrics of the invention. In this regard, included among the barrier element nonwoven fabrics of the invention are those for which the fabric has a density of about 0.08 g/cc, and is prepared from fiber having a dpf value of about 2.0. Also included are those for which the fabric has a density of about 0.08 g/cc, and comprises about 50/50 percent by weight each of about 1.0 and about 1.6 dpf fiber. Yet additionally included are those for which the fabric has a density of about 0.08 g/cc, and comprises about 50/50 percent by weight each of about 1.0 and about 2.0 dpf fiber.

Further with respect to fiber denier and fabric density, in the third preferred embodiment of the protective article of the invention, the barrier element nonwoven fabric preferably has a density of about 0.01 to 0.15 g/cc—more preferably about 0.05. to 0.15 g/cc, and still more preferably about 0.07 to 0.15 g/cc. Also as a matter of preference, in this third embodiment at least about 10 percent—more preferably at least about 20 percent, still more preferably at least about 40 percent, and yet more preferably at least about 50 percent—by weight of the staple fibers have a dpf value of not more than about 2.0.

With respect to particular suitable combinations of fiber denier and fabric weights for the barrier elements of the invention—including those of the first, second, and third embodiments—preferably, the fibers are not more than about 2.0 dpf—more preferably, not more than about 1.8 dpf—and the fabrics preferably have a corresponding fabric weight of at least about 10 gsy. As a preferred combination of denier and weight ranges, the fiber is about 0.5–2.0 dpf with a corresponding fabric weight of about 10–40 gsy. Regarding the manipulation of denier and fabric weight to obtain the requisite pore size, combinations of these parameters are preferably such as to produce a pore size less than or equal to about 52 microns, as earlier discussed. A preferred range to be provided is about 17–52 microns—likewise, as earlier discussed.

As more preferable combinations of fiber denier and fabric weight, the fibers are not more than about 1.8 dpf, with the fabric weight being at least about 20 gsy. Corresponding more preferable ranges are about 1–1.6 dpf and 15–20 gsy. The pore size produced by these more preferable combinations is correspondingly more preferably less than or equal to about 45 microns, with the accordingly more preferred range being about 17–40 microns.

Regarding particularly preferred combinations of fiber denier and fabric weight, the fibers are not more than about 1.4 dpf, with the fabric weight being at least about 15 gsy. Corresponding particularly preferred ranges are about 0.5–1.2 dpf and 10–18 gsy. The pore size produced by these particularly preferred combinations is correspondingly particularly preferably less than or equal to about 17 microns with the accordingly more preferred range being about 17–30 microns.

The fabrics of the invention—preferably, the thermally bonded fabrics—preferably give runoff values, calculated in the manner as set forth herein, greater than 90 percent, or about 90 percent. Yet another means, for defining the fabrics of the invention, is by hydrostatic head value.

Hydrostatic head is understood as quantifying the resistance of fabrics or fibers, to the penetration of a particular liquid—e.g., water, or synthetic urine—in a column, under static pressure; hydrostatic head measures the amount of liquid pressure, at atmospheric pressure, that the material will endure before it leaks—in terms of the height that the liquid column will attain, without penetration of the material. In this regard, the higher the rising liquid column, the greater the resistance of the material to liquid penetration—and, accordingly, the higher the hydrostatic head value.

Two factors affecting this value include the repellency of the fibers to the liquid used, and the fabric construction. A suitable means, for determining hydrostatic head value, is by mounting a test specimen under a column of the liquid, and subjecting the specimen to the liquid pressure,, increasing at a constant rate, until a drop of the liquid penetrates through the specimen.

Hydrostatic head value can vary, according to the liquid used for making the measurement; for instance, water gives higher hydrostatic head values, than synthetic urine. Where synthetic urine is used, the value is identified herein as synthetic urine hydrostatic head value.

In this regard, it is understood that synthetic urine is a standardized substance in the waste containment article art, with a specific uniform composition and properties (e.g., surface tension), regardless of its source. Particularly as to surface tension, it is further understood that this property can decay, over a period of time, and that it may be necessary to test the synthetic urine being used, to ensure that its surface tension is at the requisite level.

A synthetic urine which may be used, for determining synthetic urine hydrostatic head value, is Syn-Urine (Part No. JA130), from Endovations Arrow, Reddin, PA. It is yet further understood that the synthetic urine hydrostatic head values, as disclosed and recited herein, are determined from the use of this synthetic urine.

Measuring hydrostatic head with water, the barrier element fabrics of the invention—including those of the first, second and third embodiments—preferably have a hydrostatic head value of at least about 60 mm. More preferably, the water hydrostatic head value is at least about 80 mm—still more preferably at least about 100 mm, and yet more preferably at least about 130 mm. As a matter of particular preference, the barrier element fabrics of the invention have a water hydrostatic head value of at least about 160 mm.

The fibers and fabrics of the invention may be prepared by conventional techniques, with the use of conventional equipment. Specifically, standard means for effecting extrusion, and subsequent processing, may be employed.

As one appropriate method, the polymer or polymers—e.g., polyolefin granules and/or pellets—can be subjected to blending—e.g., mechanical blending, such as by dry mixing—or to both blending and melting, before being fed to the extruder. Alternatively, the polymer or polymers can simply be fed to the extruder, without such prior blending.

In the extruder, the polymer or polymers are subjected to blending, melting, and heating, then extruded therefrom, in the form of filaments. Such extrusion, with the subsequent processing, may be effected in both a two step "long spin" process, as well as in a one step "short spin" process; in this regard, it is understood that the terms "short spin" and "long spin" are used herein, in accordance with their commonly understood meanings in the art.

Specifically, known processes for making staple fiber include the two-step "long spin" process and the one-step "short spin" process. The long spin process involves first melt-extruding fibers at typical spinning speeds of 500 to 3000 meters per minute, and more usually depending on the polymer to be spun from 500 to 1500 meters per minute. Additionally, in a second step usually run at 100 to 250 meters per minute, these fibers are drawn, crimped, and cut into staple fiber. The one-step short spin process involves conversion from polymer to staple fibers in a single step where typical spinning speeds are in the range of 50 to 200 meters per minute. The productivity of the one-step process is increased with the use of about 5 to 20 times the number of capillaries in the spinnerette compared to that typically used in the long spin process. For example, spinnerettes for a typical commercial "long spin" process would include approximately 50–4,000 capillaries, and spinnerettes for a typical commercial "short spin" process would include approximately 500 to 100,000 capillaries. Typical temperatures for extrusion of the spin melt in these processes are about 250°–325° C. (For processes wherein bicomponent filaments are being produced, the numbers of capillaries refers to the number of filaments being extruded, and usually not the number of capillaries in the spinnerette.) Preferred processes for making the staple fiber are described in U.S. Pat. No. 5,281,378, and in U.S. applications Ser. Nos. 08/003,696, filed Jan. 13, 1993, 07/683,635, filed Apr. 11, 1991 (allowed), 07/939,857, filed Sep. 2, 1992 (allowed), and 08/080,849, filed Jun. 24, 1993, this last application being incorporated herein in its entirety, by reference thereto.

Regarding the foregoing, whether short spin or long spin is employed, the thusly extruded filaments are drawn, crimped, then cut, to obtain hydrophobic staple fibers, of the selected denier. So that the staple fibers will be hydrophobic and cardable, a suitable hydrophobic finish composition or compositions may be applied to the filament during processing —e.g., before, during, and/or after one or more of the extrusion, drawing, and crimping stages; preferably, a hydrophobic finish is applied during spinning, and additional finish is applied after crimping.

Preferably, a hydrophobic finish is applied to the fiber, which finish preferably comprises an antistat and lubricant. The finish may be applied as a spin finish, overfinish, or both of these. One preferred finish comprises an amine salt or an alkali metal salt of a phosphoric acid ester, and a polysiloxane. Such finishes are described in U.S. Pat. No. 4,938,832 and in European Patent Application 0 486 158.

As a preferred procedure, the following is effected:
(a) the spun filament, prior to-drawing, is treated with an effective amount—preferably, about 0.09%–0.6% based on fiber weight—of a first modifier composition (spin finish), comprising:
(i) 0% to about 40% (more preferably, about 20% to about 40%). by weight of at least one neutralized phosphoric acid ester antistat, represented by the formula

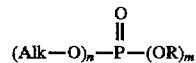

wherein Alk is individually defined as an alkyl group, preferably a 1–8 carbon alkyl group, and more preferably a 1–4 carbon alkyl group; R is defined as an amine salt or an alkali metal salt; n and m are individually defined as positive numbers of not less than about 1, the sum of which is about 3; and (ii) about 60%–100% by weight of at least one polysiloxane lubricant, represented by the formula

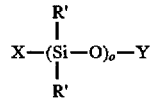

wherein X and Y are individually defined as a hydrophobic chemical end group, such as a lower alkyl group; R' is individually defined as an alkyl group, preferably a methyl group; and o is defined as a positive number within the range of about 10–50 or higher;

(b) after crimping, the filament is treated with an effective amount—preferably,—about 0.05%–0.8% by fiber weight—of a second modifier composition (an overfinish), comprising:
(i) about 50%–100% by weight of an antistat, as defined above; and
(ii) 0% to about 50% by weight of a lubricant, as defined above, in sufficient amount to obtain a final cumulative concentration within a range of about 0.01% to 1%, and preferably 0.03%–0.8%, based on fiber weight.

As a matter of particular preference, the spin finish is a mixture of the indicated antistat and lubricant, and the overfinish includes—the antistat alone—without the lubricant. A preferred antistat is Lurol ASY, from George A. Goulston Co., Monroe, N.C.; correspondingly, silicones are the preferred lubricants, one such being LE-458HS, from Union Carbide Chemical and Plastics Company Inc., Danbury, Conn.

Other preferred hydrophobic finishes are those as disclosed in U.S. application Ser. No. 08/016,346, filed Feb. 11, 1993, and in European Patent Application No. 0 516 412.

Hydrophobic and cardable fibers of the invention can be used to prepare the requisite hydrophobic fabric of the invention—particularly, nonwoven fabric.

Specifically, the fibers can be made into webs, by such a procedure as carding. With reference to the discussion herein concerning preparation of the fabrics from fibers of differing dpf values and/or differing polymer compositions, thusly differing staple fibers can be mixed together, then subjected to the carding procedure to obtain the requisite webs.

The thusly prepared webs can be subjected to bonding; in this regard, a single web can be bonded by itself (e.g., to obtain a single layer barrier cuff fabric of the invention), or two or more webs can be bonded together, to obtain a multiple layer fabric. The bonding is preferably effected by thermal techniques, such as calender or through-air bonding—thusly to obtain the nonwoven fabrics of the requisite selected fabric weights. This processing can be conducted at commercial line speeds, to produce the barrier cuff fabrics of the invention.

As discussed herein, composite or multiple layer barrier cuff fabrics of the invention—particularly, nonwoven fabrics—can be provided from two or more layers of fibers. As noted, the indicated fiber webs can be used to provide the requisite layers—for instance, by thermally bonding multiple webs according to the techniques discussed herein, to obtain the composite fabrics.

Fabrics obtained according to the procedures set forth herein can be employed as, or used to prepare, the filmless barrier cuffs for the waste containment articles of the invention. In this regard, the fabrics can be provided to the articles as the requisite cuffs; the waste containment articles themselves can be prepared by conventional means.

The invention—including the fibers and fabrics, and particularly the barrier cuff fabrics, of the invention—is illustrated in the following Examples, which are provided for the purpose of representation, and are not to be construed as limiting the scope of the invention. Unless stated otherwise, the fibers of these Examples were made at production rates, in a full size plant; also unless stated otherwise, all percentages, parts, etc. are by weight.

TESTING PROCEDURES EMPLOYED FOR FIBERS AND FABRICS OF THE EXAMPLES

The following testing procedures were employed for determining properties of fibers and fabrics of the Examples.

1. Fabric Runoff Test

A 27.5×12.5 centimeter sample of the calendered fabric, with rough face up, is placed over two sheets of Eaton-Dikeman #939 paper, 12.5×26.9 centimeters long. The sample and two sheets of paper are placed on a board with an incline of 10°, and with the sample oriented so that the longer side is in the direction of the incline. The tip of a separatory funnel is positioned 2.5 centimeters from the top of the fabric, and 2.5 centimeters above the fabric at the center of the sample; a paper towel of known weight is placed across and 0.625 centimeters from the bottom of the sample.

The separatory funnel is then filled with 25 milliliters of synthetic urine. The stopcock of the thusly filled funnel is opened; the resulting runoff is collected on the paper towel, which is weighed to the nearest 0.1 gram.

The foregoing procedure is repeated five times, and the average liquid runoff from the fabric is reported as percent runoff. The higher the percent runoff value, the greater the fabric hydrophobicity.

Results of this test are provided in Table 4, for the Examples as set forth therein.

2. Hydrostatic Head Test

This procedure employs a modified "Suter" apparatus, as an alterative to the AATCC 1952-18 British Standard 2823 apparatus.

The hydrostatic pressure is applied to the top of the sample, and is controlled by a rising water column at a constant rate of 290 cc/minute. This test can be employed with both fiber and fabric.

For the former, a five gram (±0.10 g) sample of dry, hand carded staple fiber is employed, with a staple fiber holder. The staple fiber holder has a 3.7 cm inside diameter, and is 3.0 cm long, with a screen in the top, and a cap with multiple holes, to allow the water to flow through. The fibers are compressed tightly in this sample holder, and the cap is placed on the column.

The diameter of the area of the fiber exposed to the column of water is 3.7 cm. A mirror is fixed so that the underside of the fiber sample can be observed, and the mirror is adjusted so that it is possible to see the multiple hole cap.

For testing fabric, a 10 cm×10 cm area sample is employed, with a fabric sample holder having the same dimensions as the fiber sample holder. The sample is placed on the fabric sample holder, which is clamped to the base of the column.

The column height above the sample screen is 60 cm×3.7 cm (inside diameter). The water is added to the column through a 0.5 cm. diameter vertical hole, 2.0 cm above the sample screen; a 0.50 cm diameter drain hole is placed 0.5 cm above the sample screen of the column, to remove the water after each test.

The procedure is begun by plugging the column drain hole. Water is pumped into the column, at the indicated rate of 290 cc/minute, until leakage occurs through the sample—i.e., until the first drop of water is observed to fall. At this point, the addition of water is immediately stopped, and the water column height is measured in millimeters (mm).

The column is then opened and drained. The wet sample is removed, and the chamber and mirror are thoroughly dried.

This procedure is repeated five times. The average, of the thusly resulting values, is reported as millimeters of liquid head height.

This test, employing water, was applied to fibers and fabric in Example 10, and to fabric in Examples 11 and 12—as subsequently discussed herein. For the indicated Examples 11 and 12, results are shown in Tables 5 and 6, respectively.

3. Modified Hydrostatic Head Test

This test is similar to the hydrostatic head test as set forth directly above, except in that it involves simulation of the conditions-to which liquid is exposed to the leg cuff in a diaper.

The apparatus employed for performing the modified hydrostatic head test is a rectangular plexiglas tank which is 25 centimeters high, 13.8 centimeters long, and 16.2 centimeters wide. This tank has a liquid containment section with dimensions of 19.38×13.8×16.2 centimeters; the tank also has a 10 centimeter wide and 5 centimeter high sample window cut into its front and centered 7.5 centimeters from the base of the apparatus.

For holding a fabric sample in place over the outside of the sample window, there is a plexiglas sample cover having dimensions of 17.5×16.25 centimeters, held in place by seven bolts with wing nuts. Two of these bolts are situated so that one is 2.5 centimeters above each top corner of the window, and three bolts are situated 9.375 millimeters below the window—one at each bottom corner, and the third in the center; the final two bolts are situated 5 centimeters below the bottom of the sample window, one below each window bottom corner. A 1 millimeter thick by 5 millimeter rubber gasket is attached to the window cover, to be situated around the window for preventing leakage.

A 20 centimeter ruler is attached to the front right side of the apparatus to measure the liquid head height. The ruler is positioned so that the zero liquid column point is at the bottom of the window; accordingly, the measurable liquid height reads from zero to 177 millimeters.

The liquid containment section is provided with an inlet for enabling liquid to be pumped in. This inlet, having a 12.5 millimeter inside diameter, is centered 5 millimeters from the bottom of the backside of the liquid containment section. A Masterflex model 7518-10 and model 7526-00 liquid pump is used to fill the apparatus.

The fabric sample is held in place at the sample window by the cover. Liquid is pumped into the liquid containment section at a rate of 540 milliliters per minute, until leakage occurs through the fabric sample.

With the ruler placed as indicated, the liquid head height is measured from the bottom of the slotted sample window to the top of the tank. The test is repeated five times, and the average, of the thusly resulting values, is reported in millimeters of liquid head height—specifically, as the synthetic urine hydrostatic head value, where the liquid used is synthetic urine.

Results of this test—specifically, time at leakage (in minutes), and synthetic urine hydrostatic head value, as set discussed above—are provided in Table 1, for the Examples as set forth therein.

4. Absorbency Time Test CASTM D-1117-79)

This test—employing the procedures of the indicated ASTMD-1117-79, which is incorporated herein in its entirety, by reference thereto—is another which measures hydrophobicity. The degree to which fibers are wet is determined by the amount of time required for five grams of a sample, loosely packed into a three gram mesh basket, to sink below the surface of water.

This test was applied to the fiber of Example 10, as discussed in that Example.

5. Diaper Leakage Test

In this test, a diaper, shaped as though it were fitted on a baby, is placed on white filter paper, and synthetic urine is applied at a rate of 540 milliliters per minute, through a tube placed in the center of the diaper. Four 60 milliliter insults of the synthetic urine are thusly applied, in four minute intervals.

Observations for leakage around the diaper leg-cuff are made after each insult. Leakage is noted by stains on the filter paper.

Results of this test are provided in Table 2, for the Examples and Controls as set forth therein. For each of the Examples, the Example fabric was employed as a barrier leg cuff, on a diaper with a commercial absorbent core; Control 1 was a Huggies® Pull Up diaper, with no leg cuffs, and Control 2 was an Ultra Pampers Phases® diaper, with film coated leg cuffs.

6. Cohesion Test CASTM D-4120-90)

This test—employing the procedures of the indicated ASTMD-4120-90, which is incorporated herein in its entirety, by reference thereto—provides an indication of the ability of fibers to hold together, by measuring the force required to slide fibers in a direction parallel to their length. Specific length of roving, Sliver, or top are drafted between two pairs of rollers, with each pair moving at a different peripheral speed.

The draft forces are recorded; test specimens are then weighed, and the linear density is calculated. Drafting tenacity, calculated as the draft resisting force per unit linear density, is considered to be a measure of the dynamic fiber cohesion.

Results of this test are provided in Table 3—in the column under the heading "Cohesion"—for the Examples as set forth therein.

7. Cross-Directional Strength (CD) Test (ASTM D1117-80)

This test—employing the procedures of the indicated ASTM D1117-80, which is incorporated herein in its entirety, by reference thereto—measures the breaking strength of fibers in the cross-direction, using the Instron (CRT-Constant Rate of Traverse Tensile Test Machine), under the following test conditions:

| | |
|---|---|
| Chart speed | 2 in. (5.0 centimeters) per minute |
| Crosshead speed | 5 in. (12.5 centimeters) per minute |
| Gauge length | 5 in. (12.5 centimeter) |
| Extension rate | 40% per minute |

The test specimens are 25 mm wide and 180 mm long, and five specimens are tested for each sample. The results are reported as the average breaking load, in grams per inch.

As with the Cohesion Test discussed directly above, results of this test are also provided in Table 3—for the specified Examples—under the heading "CD Strength".

EXAMPLE 1

Polypropylene fibers were prepared using a two step process. The polymer mixture which was employed contained polypropylene, 0.10% Irgafos 168 (Ciba Geigy Corporation, Ardsley, N.Y.), and 0.20% titanium oxide.

In the first step, these components were thoroughly mixed, then gravity fed into an extruder; therein, the mixture was heated, then extruded, and spun into a circular cross-sectional, multifilament fiber, at a melt temperature of 280° to 300° C. Prior to melting, at the feed throat of the extruder, the mixture was blanketed with nitrogen.

The melt was extruded through a standard 1068 hole spinnerette, at a rate of 759 meters per minute, to make a 3.0 dpf (3.3 dtex) filament; the molten filaments were quenched one inch from the face of the spinnerette. A hydrophobic spin finish mixture was applied to the spun fiber, in an amount so as to provide 0.30% of the total weight, determined as dry weight, of the resulting treated fiber; this spin finish consisted of a 1:3 mixture of antistat (Lurol ASY, from George A. Goulston Co.) and silicone lubricant (LE-458HS, from Union Carbide Chemical and Plastics Company Inc.), diluted to a 3.0% mixture of solids in water.

In the second step, the resulting continuous filaments were collectively drawn to a 2.2 dpf (2.42 dtex), using a 1.65× mechanical draw ratio, with 90% effective draw. The drawn tow was crimped at about 113.97 crimps per 10 cm (29 crimps per inch) using a stuffer box with steam; in this regard, the fibers were crimped so as to have enough cohesion for carding purposes. After the crimping, additional Lurol was added to the fibers, in an amount so as to provide 0.1% of the total weight, determined as dry weight, of the resulting treated fibers; the fibers were then cut into staple fiber, having lengths of 37.5 mm.

A card and bond procedure was then employed with this staple fiber, using equipment and procedures as discussed in LEGARE, R. J., "Thermal Bonding of Polypropylene Fibers in Nonwovens," 1986 TAPPI Synthetic fibers for Wet System and Thermal Bonding Applications, Boston Park Plaza Hotel & Towers, Boston, Mass., Oct. 9–10, 1986. This article is incorporated herein in its entirety, by reference thereto.

In this procedure, the staple was carded into conventional fiber webs at line speeds of 76.25 meters per minute (250 feet per minute). Three of these webs were oriented and stacked, to form a single web, having a weight of 23 gsy (27.6 gsm).

The web was then bonded, using a diamond design embossed calender roll and a smooth roll, at roll temperatures ranging from 156° to 175° C., and roll pressures of 420 Newtons per linear centimeter (240 pounds per linear inch). The thusly calendered web was converted into a fabric, of the indicated 23 gsy (27.6 gsm) fabric weight; for the tests employing fabric, it was cut into test specimens.

The fiber and fabric of Example 1 were determined to be hydrophobic, as demonstrated by the data set forth in Tables 1 and 4 (in this regard, fabric with poor hydrophobicity would have a hydrostatic head of 30 milliliters or less).

Table 2 shows the results of testing two different diapers, each with Example 1 fabric used as a diaper barrier leg cuff. In both instances, there was no leakage around the leg cuff, after four 60 milliliter doses of synthetic urine.

Physical properties, of the Example 1 fiber and fabric, are provided in Table 3, and in the indicated Table 4.

EXAMPLE 2

For this Example, fibers and fabric were prepared by the spinning, processing, and calender bonding procedures as set forth in Example 1, except that the fabric was provided with a fabric weight of 20 gsy (24 gsm). As evidenced by the hydrostatic head and runoff values set forth in Tables 1 and 4, the thermal bonded fabric gave good hydrophobicity.

EXAMPLE 3

The fiber and fabric in this Example were also prepared as in Example 1, except that the fabric weight provided was 17 gsy (20.4 gsm). Here also, the liquid hydrostatic head and percent runoff values, in Tables 1 and 4, demonstrate that the thermal bond fabric from this fiber was hydrophobic and gave good hydrophobicity. As with Example 1, Table 2 shows that tests of two different diapers, with leg cuffs of this barrier uncoated fabric, gave no leakage around the leg cuff, after four doses with 60 milliliters of synthetic urine.

EXAMPLE 4

For this Example, spinning, processing, and calender bonding were effected as in Example 1, except that the spun fiber was processed into 1.8 dpf (1.98) dtex) staple fiber, and the draw ratio employed, during processing oft his fiber, was 1.90×; as in Example 1, the weight, of the ultimately obtained thermal bonded fabric, was 23 gsy (27.6 gsm). This fabric also gave good hydrophobicity, as shown by the liquid hydrostatic head and percent runoff values in Tables 1 and 4.

EXAMPLE 5

For this Example, the fiber is the same as that of Example 4; the fabric, however, was prepared with a weight of 20 gsy (24 gsm). The values provided in Tables 1 and 4 here also demonstrate that the fabric gave good hydrophobicity.

EXAMPLE 6

The fiber in this Example is also the same as that of Example 4; but in this instance, the fabric was prepared with a weight of 17 gsy (20.4 gsm). The values provided in Tables 1 and 4 in this instance also demonstrate that the fabric gave good hydrophobicity.

EXAMPLE 7

For this Example, spinning, processing, and calender bonding were effected as in Example 1, except that the spun fiber was processed into 1.6 dpf (1.76 dtex) staple fiber, and the draw ratio employed, during processing of this fiber, was 2.24×. As in Example 1, the fabric weight, of the ultimately obtained thermal bonded fabric, was 23 gsy (27.6 gsm).

The values provided in Tables 1 and 4 again demonstrate that the fabric gave good hydrophobicity. As with Examples 1 and 3, Table 2 shows that tests of two different diapers, with leg cuffs of this fabric, gave no leakage around the leg cuff, after four doses with 60 milliliters of synthetic urine.

EXAMPLE 8

For this Example, the fiber is the same as that of Example 7; the fabric, however, was prepared with a weight of 20 gsy (24 gsm). The fabric featured good hydrophobicity, as can be seen in Tables 1 and 4. As with Examples 1, 3, 7, and 8, Table 2 shows that tests of two different fabric, with leg cuffs of this fabric, gave no leakage around the leg cuff, after four doses with 60 milliliters of synthetic urine.

EXAMPLE 9

For this Example, is also the same as that of Example 7; in this instance, however, the fabric was prepared with a weight of 17 gsy (20.4 gsm). The results provided in Table 1 here also demonstrate good hydrophobicity.

EXAMPLE 10

Here, a pilot scale plant was employed. The polypropylene fibers were spun into a 2.38 dpf (2.618 dtex) filament, to which 0.30% of a hydrophobic spin finish mixture —the same as that of Example 1—was applied.

The spun fiber was processed into a 1.6 dpf (1.76 dtex) staple fiber, by drawing the spun fiber at a 1.65 draw ratio with 90% effective draw; an additional 0.10% Lurol ASY was added to the drawn fibers after crimping. The staple was carded and calender thermal bonded at line speeds of 250 feet per minute (76.2 meter per minute), into a 23 gsy (27.6 gsm) fabric.

For this Example, the liquid used, for determining hydrostatic head value, was water. In this regard, the water hydrostatic head value for the fiber was determined to be 272 millimeters; for the fabric, 122 millimeters. The sink time, for the fiber, was over 24 hours.

EXAMPLE 11

For this Example, the procedures of Example 1 were employed, except as set forth herein.

For instance, the filament obtained by extrusion from the spinnerette was 2.8 dpf (3.08 dtex). Further, in the second step of the two part process for fiber preparation, a mechanical draw ratio of 2.8x was employed, and the filaments were drawn to different desired deniers; correspondingly, in the card and bond operation, the single webs and resulting fabric were likewise of varying desired weights. The deniers of the fibers thusly obtained, and the weights of the fabrics prepared from these fibers, are set forth in Table 5.

Specifically, as shown in Table 5, the fabrics were of weights ranging from 16.4 to 23.3 gsy (19.7 to 28.0 gsm), and were prepared from fibers of 1.0 to 2.2 dpf (1.1 to 2.42 dtex); these fabrics were cut into test specimens and identically tested for hydrophobicity with water, using the first-provided hydrostatic head test herein—i.e., the indicated modification of AATCC 1952-18.

The results of this testing are likewise shown in Table 5. As evidenced by the data provided in this Table, the combination of lower denier fibers, with higher fabric weights, results in higher hydrostatic head values.

EXAMPLE 12

For this Example the fibers, fabrics, and specimens were prepared and tested as in Example 11, except that fibers of two different deniers—i.e., 1.0 dpf (1.1 dtex) and 1.6 dpf (1.76 dtex) were prepared, and the fabrics were made from blends of these fibers. In the preparation of the fabrics, staple fibers of the different deniers were mixed, then subjected to the card and bond procedure; different relative proportions of the different denier fibers were employed, and the fabrics prepared from these different blends all had a fabric weight of 20 gsy.

The data for this Example are provided in Table 6. As is evident therefrom, the fabric hydrostatic head increased, with increased levels of 1.0 dpf fibers in the fabric.

TABLE 1

FABRIC HYDROPHOBICITY AS MEASURED BY SYNTHETIC URINE USING MODIFIED HYDROSTATIC HEAD TEST

| Examples | Fabric Weight (gsy) | Fiber Denier (dpf) | Time At Leakage (min.) | Hydrostatic Head Height At Leakage (mm.) |
|---|---|---|---|---|
| 1 | 23 | 2.2 | 3.9 | 93 |
| 2 | 20 | 2.2 | 3.4 | 89.4 |
| 3 | 17 | 2.2 | 3.1 | 74.2 |
| 4 | 23 | 1.8 | 3.7 | 96.2 |
| 5 | 20 | 1.8 | 3.4 | 86 |
| 6 | 17 | 1.8 | 2.7 | 64.6 |
| 7 | 23 | 1.6 | 3.9 | 101 |
| 8 | 20 | 1.6 | 3.5 | 90.2 |
| 9 | 17 | 1.6 | 3.4 | 79.4 |

TABLE 2

DIAPER LEAKAGE DATA

| Examples | Type Leg-cuff | Milliliter Synthetic Urine Per Insult | Occurrence Of Leakage Around Leg-Cuff |
|---|---|---|---|
| Control 1 | none | 60 | none |
| | | 60 | leakage |
| | | 60 | leakage |
| | | 60 | leakage |
| Control 2 | fabric + film | 60 | none |
| | | 60 | none |
| | | 60 | none |
| | | 60 | none |
| Example 1 | fabric only | 60 | none |
| | | 60 | none |
| | | 60 | none |
| | | 60 | none |
| Example 1 repeated | fabric only | 60 | none |
| | | 60 | none |
| | | 60 | none |
| | | 60 | none |
| Example 3 | fabric only | 60 | none |
| | | 60 | none |
| | | 60 | none |
| | | 60 | none |
| Example 3 repeated | fabric only | 60 | none |
| | | 60 | none |
| | | 60 | none |
| | | 60 | none |
| Example 7 | fabric only | 60 | none |
| | | 60 | none |
| | | 60 | none |
| | | 60 | none |
| Example 7 repeated | fabric only | 60 | none |
| | | 60 | none |
| | | 60 | none |
| | | 60 | none |
| Example 8 | fabric only | 60 | none |
| | | 60 | none |
| | | 60 | none |
| | | 60 | none |
| Example 8 repeated | fabric only | 60 | none |
| | | 60 | none |
| | | 60 | none |
| | | 60 | none |

TABLE 3

FABRIC AND FIBER PROPERTIES

| Examples | Denier/ Filament | Crimps/ Inch | Cohesion | Fabric Wt. (gsv) | CD Strength |
|---|---|---|---|---|---|
| 1 | 2.2 | 25 | 5.5 | 23 | 548 |
| 2 | 2.2 | " | " | 20 | 454 |
| 3 | 2.2 | " | " | 17 | 340 |
| 4 | 1.8 | 26 | 5.8 | 23 | 586 |
| 5 | 1.8 | " | " | 20 | 480 |
| 6 | 1.8 | " | " | 17 | 397 |
| 7 | 1.6 | 28 | 6.9 | 23 | 454 |
| 8 | 1.6 | " | " | 20 | 451 |
| 9 | 1.6 | " | " | 17 | 406 |

TABLE 4

FABRIC AND FIBER HYDROPHOBICITY PROPERTIES

| Examples | % Fabric Runoff |
|---|---|
| 1 | 95 |
| 2 | 96 |
| 3 | 97 |
| 4 | 96 |

TABLE 4-continued

FABRIC AND FIBER HYDROPHOBICITY PROPERTIES

| Examples | % Fabric Runoff |
|---|---|
| 5 | 97 |
| 6 | 97 |
| 7 | 98 |
| 8 | 96 |

TABLE 5

| Denier Per Filament | Basis Weight GSY | Hydrostatic Head MM |
|---|---|---|
| 1 | 16.8 | 128 |
| 1 | 17.9 | 122 |
| 1 | 18.7 | 125 |
| 1 | 19.9 | 110 |
| 1 | 20.7 | 139 |
| 1 | 22.0 | 155 |
| 1 | 23.2 | 167 |
| 1.3 | 16.9 | 115 |
| 1.3 | 18.0 | 103 |
| 1.3 | 18.9 | 103 |
| 1.3 | 20.1 | 121 |
| 1.3 | 21.0 | 120 |
| 1.3 | 22.1 | 123 |
| 1.3 | 23.1 | 131 |
| 1.6 | 16.6 | 72 |
| 1.6 | 17.8 | 79 |
| 1.6 | 19.0 | 88 |
| 1.6 | 20.0 | 98 |
| 1.6 | 21.1 | 102 |
| 1.6 | 22.0 | 112 |
| 1.8 | 16.4 | 77 |
| 1.8 | 18.1 | 91 |
| 1.8 | 18.7 | 90 |
| 1.8 | 19.8 | 96 |
| 1.8 | 20.9 | 98 |
| 1.8 | 22.3 | 116 |
| 1.8 | 23.3 | 102 |
| 2.2 | 17.1 | 76 |
| 2.2 | 17.6 | 68 |
| 2.2 | 19.0 | 72 |
| 2.2 | 19.9 | 80 |
| 2.2 | 20.9 | 73 |
| 2.2 | 22.3 | 91 |
| 2.2 | 23.1 | 76 |

TABLE 6

HYDROSTATIC HEAD OF 20 GSY FABRICS FROM BLENDS OF 1.0 AND 1.6 DPF FIBER

| PERCENT 1.6 DPF | PERCENT 1.0 DPF | Hydrostatic Head MM |
|---|---|---|
| 100 | 0 | 88 |
| 95 | 5 | 90 |
| 90 | 10 | 92 |
| 85 | 15 | 94 |
| 80 | 20 | 96 |
| 75 | 25 | 98 |
| 70 | 30 | 100 |
| 65 | 35 | 102 |
| 60 | 40 | 104 |
| 55 | 45 | 106 |
| 50 | 50 | 108 |
| 45 | 55 | 110 |
| 40 | 60 | 112 |
| 35 | 65 | 114 |
| 30 | 70 | 116 |
| 25 | 75 | 118 |
| 20 | 80 | 120 |
| 15 | 85 | 123 |
| 10 | 90 | 125 |
| 5 | 95 | 127 |
| 0 | 100 | 129 |

This application is related to British Provisional Application No. 93-174902, filed Aug. 23, 1993, from which priority is claimed, and which is incorporated herein in its entirety, by reference thereto.

Finally, although the invention has been described with reference to particular means, materials, and embodiments, it should be noted that the invention is not limited to the particulars disclosed, and extends to all equivalents within the scope of the claims.

What is claimed is:

1. A waste containment article comprising a filmless hydrophobic barrier element selected from the group consisting of barrier cuffs and fluid-impervious backing components, the filmless hydrophobic barrier element comprising a nonwoven fabric comprising carded and bonded hydrophobic polyolefin staple fibers, substantially all of the staple fibers having a dpf value of not more than about 2.0, and:

(1) having a water hydrostatic head value of at least about 60 mm; and
 (2) having a fabric weight of at least about 10 gsy.

2. The article of claim 1 wherein substantially all of the staple fibers have a dpf value of not more than about 1.8.

3. The article of claim 1 wherein the nonwoven fabric has an average pore size of not more than about 52 microns.

4. The article of claim 1 wherein the staple fibers comprise a polyolefin having a hydrophobic antistatic finish.

5. The article of claim 4 wherein the polyolefin comprises polypropylene, and wherein substantially all of the staple fibers are about 1 to 3 inches in length.

6. The article of claim 1 wherein the polyolefin comprises polypropylene.

7. The article of claim 1 which is a diaper, wherein the filmless hydrophobic barrier element comprises at least one member selected from the group consisting of leg cuffs, waistbands, and fluid-impervious backing components.

8. The article of claim 1 which is selected from the group consisting of shirts, pants, jackets, coats, hospital and surgical caps, hospital and surgical gowns, hospital and surgical scrub apparel, sheets, surgical table covers, Mayo stand covers, industrial garments, catamenial devices, and incontinence pads.

9. A protective article comprising a filmless hydrophobic barrier element, wherein the filmless hydrophobic barrier element comprises a nonwoven fabric having a water hydrostatic head value of at least about 60 mm and comprising carded and bonded hydrophobic polyolefin staple fibers, at least about 10 percent by weight of the staple fibers having a dpf value of not more than about 2.0.

10. The article of claim 9 which is a waste containment article.

11. The article of claim 10 wherein the filmless hydrophobic barrier element comprises at least one member selected from the group consisting of barrier cuffs and fluid-impervious backing components.

12. The article of claim 11 wherein at least about 30 percent by weight of the staple fibers have a dpf value of not more than about 2.0.

13. The article of claim 12 wherein at least about 40 percent by weight of the staple fibers have a dpf value of not more than about 2.0.

14. The article of claim 13 wherein at least about 50 percent by weight of the staple fibers have a dpf value of not more than about 2.0.

15. The article of claim 11 wherein the nonwoven fabric has a basis weight of about 10–50 gsy.

16. The article of claim 11 wherein the staple fibers comprise a hydrophobic antistatic finish.

17. The article of claim 16 wherein the polyolefin comprises polypropylene, and wherein substantially all of the staple fibers are about 1 to 3 inches in length.

18. The article of claim 11 wherein the polyolefin comprises polypropylene.

19. The article of claim 11 wherein the staple fibers comprise fibers of at least two different dpf values.

20. The article of claim 19 wherein about 10 to 90 percent by weight of the staple fibers have a dpf value of about 0.5 to 2.0, and about 10 to 90 percent by weight of the staple fibers have a dpf value of about 2.2 to 4.0 dpf.

21. The article of claim 19 wherein about 10 to 90 percent by weight of the staple fibers have a dpf value of about 1.0 to 1.8, and about 10 to 90 percent by weight of the staple fibers have a dpf value of about 2.2 to 4.0 dpf.

22. The article of claim 19 wherein the nonwoven fabric comprises a layer comprising the fibers of at least two different dpf values.

23. The article of claim 19 wherein the nonwoven fabric comprises at least two layers, a first layer of the at least two layers comprising fibers having a first dpf value and a second layer of the at least two layers comprising fibers having a second dpf value, the first dpf value being different from the second dpf value.

24. The article of claim 23 wherein the nonwoven fabric is a two layer fabric consisting essentially of the first layer and the second layer.

25. The article of claim 23 wherein the first dpf value is about 0.5 to 2.0 and the second dpf value is about 2.2 to 4.0, about 10 to 90 percent by weight of the staple fibers having the first dpf value and about 10 to 90 percent by weight of the staple fibers have the second dpf value.

26. The article of claim 25 wherein the polyolefin comprises polypropylene, and wherein substantially all of the staple fibers are about 1 to 3 inches in length.

27. The article of claim 25 wherein the staple fibers comprise a hydrophobic antistatic finish.

28. The article of claim 27 wherein the polyolefin comprises polypropylene, and wherein substantially all of the staple fibers are about 1 to 3 inches in length.

29. The article of claim 23 wherein the first dpf value is about 1.0 to 1.8 and the second dpf value is about 2.2 to 4.0, about 10 to 90 percent by weight of the staple fibers having the first dpf value and about 10 to 90 percent by weight of the staple fibers have the second dpf value.

30. The article of claim 22 wherein about 10 to 90 percent by weight of the staple fibers have a dpf value of about 0.5 to 2.0, and about 10 to 90 percent by weight of the staple fibers have a dpf value of about 2.2 to 4.0 dpf.

31. The article of claim 30 wherein the staple fibers comprise a polyolefin having a hydrophobic antistatic finish.

32. The article of claim 31 wherein the polyolefin comprises polypropylene, and wherein substantially all of the staple fibers are about 1 to 3 inches in length.

33. The article of claim 30 wherein the polyolefin comprises polypropylene, and wherein substantially all of the staple fibers are about 1 to 3 inches in length.

34. The article of claim 22 wherein about 10 to 90 percent by weight of the staple fibers have a dpf value of about 1.0 to 1.8, and about 10 to 90 percent by weight of the staple fibers have a dpf value of about 2.2 to 4.0 dpf.

35. The article of claim 19 which is a diaper, wherein the filmless hydrophobic barrier element comprises at least one member selected from the group consisting of leg cuffs, waistbands, and fluid-impervious backing components.

36. The article of claim 19 which is selected from the group consisting of shirts, pants, jackets, coats, hospital and surgical caps, hospital and surgical gowns, hospital and surgical scrub apparel, sheets, surgical table covers, Mayo stand covers, industrial garments, catamenial devices, and incontinence pads.

37. A waste containment article comprising:
   (a) a fluid-impervious backing component, comprising a filmless hydrophobic barrier element;
   (b) a body-contacting surface; and
   (c) a fluid-adsorbing component situated between the fluid-impervious backing component and body-contacting surface;
   wherein the filmless hydrophobic barrier element comprises a nonwoven fabric:
      having a water hydrostatic head value of at least about 60 mm; and
      comprising carded and bonded hydrophobic polyolefin staple fibers, at least about 10 percent by weight of the staple fibers having a dpf value of not more than about 2.0;
   wherein the staple fibers comprise fibers of at least two different dpf values;
   wherein the nonwoven fabric comprises at least two layers:
      a first layer of the at least two layers comprising fibers having a first dpf value; and
      a second layer of the at least two layers being situated between the first layer and the fluid-adsorbing component, and comprising fibers having a second dpf value, the first dpf value being different from the second dpf value; and
   wherein the first dpf value is about 2.2 to 4.0 and the second dpf value is about 0.5 to 2.0, about 10 to 90 percent by weight of the staple fibers having the first dpf value and about 10 to 90 percent by weight of the staple fibers have the second dpf value.

* * * * *